United States Patent [19]
Cole

[11] Patent Number: 5,836,993
[45] Date of Patent: Nov. 17, 1998

[54] ELECTROTHERAPY DEVICE CONTROL SYSTEM AND METHOD

[75] Inventor: Clinton S. Cole, Seattle, Wash.

[73] Assignee: Heartstream, Inc., Seattle, Wash.

[21] Appl. No.: 648,776

[22] Filed: May 16, 1996

[51] Int. Cl.$^6$ ...................................................... A61N 1/08
[52] U.S. Cl. .................................. 607/59; 607/30; 607/2
[58] Field of Search ................................ 607/2, 5, 4, 30, 607/31, 32, 48, 60, 59

[56] References Cited

U.S. PATENT DOCUMENTS

| | | | |
|---|---|---|---|
| 4,832,033 | 5/1989 | Maher et al. | 607/2 |
| 4,919,139 | 4/1990 | Brodard | 607/59 |
| 5,033,469 | 7/1991 | Brodard | 607/59 |
| 5,072,730 | 12/1991 | Lee | 607/59 |
| 5,285,781 | 2/1994 | Brodard | 607/59 |
| 5,441,528 | 8/1995 | Chang et al. | 607/59 |
| 5,443,486 | 8/1995 | Hrdlicka et al. | 607/59 |

FOREIGN PATENT DOCUMENTS

WO 94/00182   1/1994   WIPO .

OTHER PUBLICATIONS

Operating instructions for Laerdal Heartstart Medical Control Unit with Multiplex Tape Format.
Marquette® Responder™ 1500 Defibrillator and cardiac care system operator's manual (16th Ed.) (1994).

*Primary Examiner*—William E. Kamm
*Assistant Examiner*—Kennedy J. Schaetzle
*Attorney, Agent, or Firm*—James R. Shay; Cecily Anne Snyder

[57] ABSTRACT

An electrotherapy device control system that improves on prior art electrotherapy device control systems by providing for operation of the electrotherapy device with software code or instructions stored on an attachable memory device. In one embodiment, the invention is a method of controlling the operation characteristics of an electrotherapy device, including the steps of providing an electrotherapy device having a controller and a first memory, the first memory containing instructions for use by the controller to operate the electrotherapy device; attaching a second memory to the electrotherapy device, the second memory containing instructions for use by the controller to operate the electrotherapy device; and operating the electrotherapy device using instructions contained only in the second memory. The invention also includes an apparatus for performing the method and a memory device for use with the apparatus.

46 Claims, 9 Drawing Sheets

ELECTROTHERAPY DEVICE CONTROL SYSTEM AND METHOD

BACKGROUND OF THE INVENTION

This invention relates generally to a control system for an electrotherapy device, such as a pacemaker, cardioverter or defibrillator. In particular, this invention relates to a method of controlling the operation characteristics of an external electrotherapy device using an external memory which has been attached to the electrotherapy device.

Electrotherapy devices are used to provide electric shocks to treat patients for a variety of heart arrhythmias. For example, external defibrillators provide relatively high-level shocks to a patient, usually through electrodes attached to the patient's torso, to convert ventricular fibrillation to a normal sinus rhythm. Similarly, external cardioverters can be used to provide shocks to convert atrial fibrillation to a more normal heart rhythm.

From time to time, it may be necessary to change the operation characteristics of the electrotherapy device, either temporarily or permanently. For example, the Laerdal Heartstart 3000 external defibrillator may be operated in either semi-automatic mode or manual mode. The operation mode of the Heartstart 3000 defibrillator may be changed from semi-automatic treatment mode to manual treatment mode by inserting a solid state memory module into a port in the defibrillator. The memory module also records information about the defibrillator's operation and segments of the patient's ECG related to defibrillator use.

As another example, the Marquette Responder 1500 external defibrillator uses a custom set-up card to set system defaults and to program the operation of the defibrillator. To use, the set-up card is inserted into a card slot in the Responder 1500 defibrillator housing. This same card slot is also used for receiving a patient data card to record patient data during a treatment operation of the defibrillator.

SUMMARY OF THE INVENTION

The present invention is an electrotherapy device control system that improves on prior art electrotherapy device control systems by providing for operation of the electrotherapy device with software code or instructions stored on an attachable memory device. In one embodiment, the invention is a method of controlling the operation characteristics of an electrotherapy device, including the steps of providing an electrotherapy device having a controller and a first memory, the first memory containing instructions for use by the controller to operate the electrotherapy device; attaching a second memory to the electrotherapy device, the second memory containing instructions for use by the controller to operate the electrotherapy device; and operating the electrotherapy device using instructions contained only in the second memory. The operating step could include operating the electrotherapy device in a training mode, in a treatment mode, in a custom operation mode, in a diagnostic mode, in a patient monitoring mode, in a set-up mode, or in a code transfer mode to replace instructions in the first memory with instructions in the second memory. The operating step could include providing information to a user in a language controlled by instructions contained in the second memory.

In one embodiment, the method includes, prior to the operating step, actuating a memory control mechanism to transfer communication between the controller and the first memory to communication between the controller and the second memory.

The attaching step could include inserting a second memory into the device or attaching the second memory to a memory port in the electrotherapy device. In the latter case, the method could also include the step of operating the electrotherapy device using instructions contained only in the first memory to write information to the memory port prior to the attaching step.

Alternatively, the attaching step could include providing communication between the second memory and the electrotherapy device, the second memory being disposed at a location remote from the electrotherapy device.

In one embodiment of the method of this invention, the electrotherapy device is a defibrillator, the first memory containing instructions for use by the controller to operate the defibrillator in a treatment mode to treat a patient.

The method may also include booting the electrotherapy device from instructions contained in the first memory or, alternatively, booting the electrotherapy device from instructions contained in the second memory. The method could also include determining whether there are executable instructions in the second memory. If so, the method may also include reading an identification in the second memory.

In another embodiment, the invention is a method of operating an electrotherapy device, including attaching a memory to a memory port in a housing of the electrotherapy device and reading instructions from the memory to operate the electrotherapy device. This method could also include the step of inserting a PC card into a card slot in the electrotherapy device.

The invention also includes a control system for an electrotherapy device including a controller; a first memory communicating with the controller, the first memory containing instructions for use by the controller to operate the electrotherapy device; and a second memory communicating with the controller via a memory port, the second memory containing instructions for use by the controller to operate the electrotherapy device without instructions from the first memory. The control system may also include means for transferring communication between the controller and the first memory to communication between the controller and the second memory, such as a memory control mechanism (e.g., a button or an actuator responsive to the attachment of the second memory to the memory port). Alternatively, the means for transferring may be instructions causing the controller to communicate with the second memory. The control system's controller and first memory may comprise means for writing information to the memory port.

In another embodiment, the invention is a control system for an electrotherapy device including a controller; a first memory communicable with the controller, the first memory containing instructions for use by the controller to operate the electrotherapy device; and means for establishing communication between the controller and a second memory and for operating the electrotherapy device using instructions from the second memory without using instructions from the first memory.

Yet another embodiment of the invention provides an electrotherapy device including a controller; an energy delivery system communicable with the controller; and a first memory communicable with the controller, the first memory containing instructions for use by the controller to operate the electrotherapy device; the controller including means for establishing communication between the controller and a second memory and for operating the electrotherapy device using instructions from the second memory without using instructions from the first memory. The electrotherapy device may also include a memory port, the means for establishing communication comprising means for establishing communication with the memory port, such as a PC card slot. The device may also include a memory control mechanism for transferring control from the first memory to the second memory.

In yet another embodiment, the invention is an electrotherapy device including a controller; an energy delivery system communicable with the controller; and a memory port; the controller comprising means for establishing communication between the controller and a memory attached to the memory port and for operating the electrotherapy device using instructions from the memory.

One embodiment of the invention is a memory device for use with an electrotherapy device including a housing; a connector adapted to connect with a memory port of an electrotherapy device; memory; control logic and a memory device identification.

The invention is also a method of operating an electrotherapy device including attaching a memory unit to a memory unit port in the electrotherapy device; determining whether the memory unit is a recording memory unit to which information may be written by the electrotherapy device and whether the memory unit is an executing memory unit from which executable code may be obtained by the electrotherapy device. The determining step may include the device reading a memory unit identification to determine whether the memory unit is a recording memory unit or an executing memory unit. The method may also include, after the determining step, writing information to the memory unit if the memory unit is determined to be a recording memory unit or obtaining operating instructions from the memory unit if the memory unit is determined to be an executing memory unit.

Yet another embodiment of the invention is an electrotherapy device including an energy source; an electrode interface; a controller operatively connected with the energy source and the electrode interface to deliver energy from the energy source to the electrode interface; a memory port; the controller including means for determining whether a memory unit attached to the memory port is a recording memory unit to which information may be written by the controller and whether the memory unit is an executing memory unit from which execution code may be obtained by the controller. The controller of the invention may include means for writing information to a memory unit attached to the memory port if the memory unit is determined to be a recording memory unit or means for obtaining operating instructions from a memory unit attached to the memory port if the memory unit is determined to be an executable memory unit. The means for determining may also include means for reading a memory unit identification from a memory unit attached to the memory port.

Finally, in yet another embodiment, the invention is a memory unit for use with an electrotherapy device, including a connector; digital memory storage; a memory unit identification identifying the memory unit as a recording memory unit to which information may be written by an electrotherapy device to which the memory unit is attached or as an executing memory unit from which executable code may be obtained by the electrotherapy device; and a bus communicating the digital memory storage and the memory unit identification to the connector.

The invention is described in more detail below with reference to the drawings.

DETAILED DESCRIPTION OF THE PREFERRED EMBODIMENTS

Modern electrotherapy devices are typically microprocessor-controlled. The code or software instructions used by the microprocessor or other controller may be stored in solid state memory within the device or within memory otherwise attached to, or associated with, the device. These instructions help govern the way in which the device operates, and, hence, the operation characteristics of the device. Our invention provides a control system and method for controlling the operation characteristics of an electrotherapy device by providing a set of instructions to be used by the controller during a treatment or other operation of the device.

Figure 1:
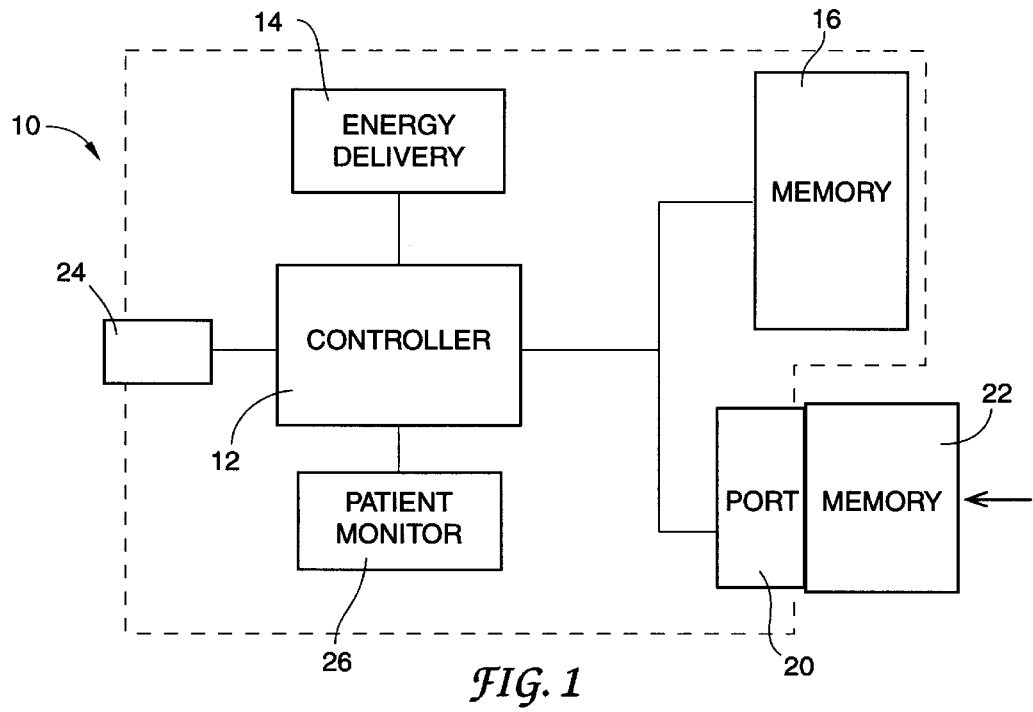
FIG. 1 is a block diagram of an electrotherapy device showing a control system according to one embodiment of this invention.
Figure 2:
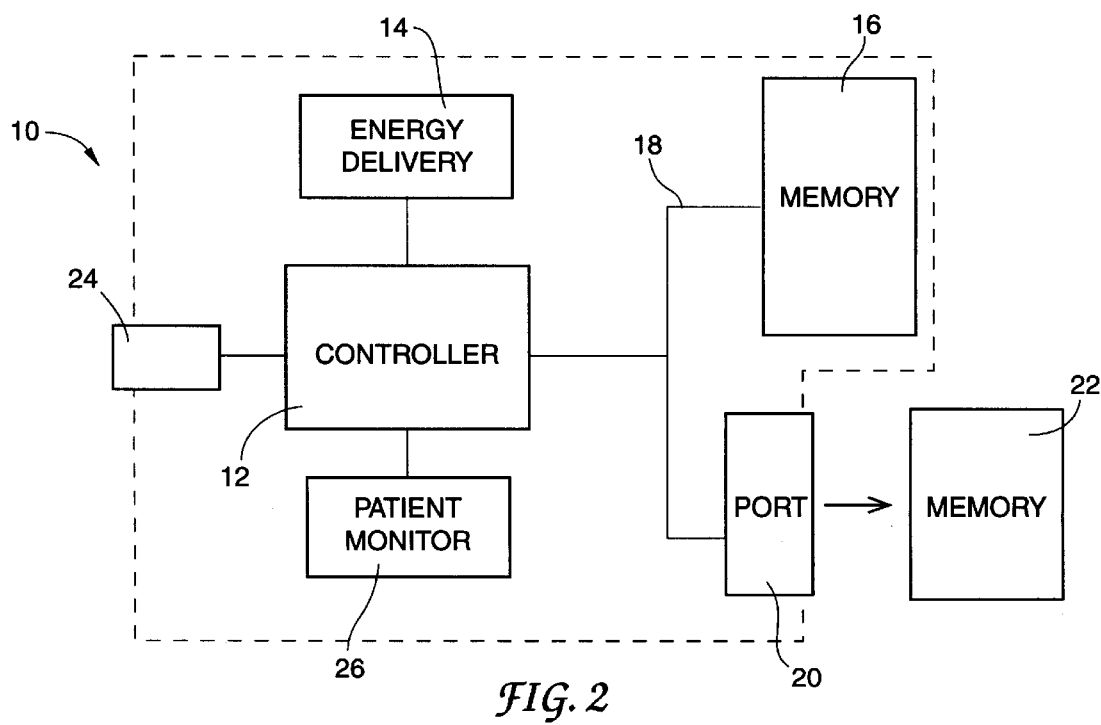
FIG. 2 is a block diagram of the embodiment of FIG. 1 with the second memory detached.

As shown schematically in FIGS. 1 and 2, one embodiment of the invention starts with a fully-functional electrotherapy device 10. Device 10 may be a defibrillator, a cardioverter, a pacer, a combination of these, or any other electrotherapy device. Device 10 has a controller 12 that operates an energy delivery system 14 and performs other aspects of the operation of the device using software instructions contained in memory 16. It should be understood that, in this and other embodiments described below, "controller" means a microprocessor, controller, gate array, other control logic, or any combination of these elements.

Controller 12 communicates with a first memory 16 via a memory bus 18. Device 10 also has a memory port 20 communicable with bus 18. A second memory 22 may be attached to device 10 via port 20, as shown in FIG. 1. Once attached, second memory 22 may communicate with controller 12 over memory bus 18. While FIG. 1 shows second memory 22 attached to device 10, memory 22 is not part of device 10 and may be subsequently detached from device 10 after use, as shown in FIG. 2.

Also, memory port 20 may be dedicated to the attachment of a second memory or it may be a more general purpose port for use in other ways as well. For example, the electrotherapy device could also write data (such as patient information or device operation information) to a memory attached to port 20.

In this embodiment, first memory 16 contains instructions sufficient to operate device 10. In other words, device 10 is fully functional before any additional memory is attached to port 20. When a second memory device (such as second memory 22 in FIG. 1) is attached to device 10 through port 20, however, controller 12 may operate device 10 from instructions in second memory 22 without using any instructions from first memory 16. In this way, the operation characteristics of device 10 may be controlled simply by attaching a second memory 22 to port 20. Likewise, device 10 may once again be operated from instructions in first memory 16, either after detachment of second memory 22 from port 20 of device 10 or while second memory 22 is still attached.

It may be necessary to actuate a memory control mechanism or a routine in order to transfer the controller's use of one memory to the other. FIGS. 1 and 2 therefore show an optional actuator 24 for a memory control mechanism. The actuator may be a button or other input separate from port 20 and second memory 22, as shown. Alternatively, the actuator may be associated with the memory port or the attachable memory so that upon attachment of the second memory (or detection of the presence of the second memory) the controller automatically transfers communication from the first memory to the attachable second memory. The transfer of communication from one memory to another may also be a strictly software operation, with the controller responding to stored instructions. Transfer of memory communication may also be accomplished through a combination of these and/or other steps.

FIG. 1 shows a single bus 18 connecting both first memory 16 and second memory 18 to controller 12. It should be understood that other communication arrangements are possible. For example, there may be two separate buses connecting the first and second memory, respectively, with the controller. Also, there may be an intervening switch or control logic between the controller and the two memories.

The electrotherapy device 10 may have an optional patient monitoring system 26 to collect patient ECG information or other patient information. The electrotherapy device may have other features, of course, which are not shown in FIGS. 1 and 2.

This invention may be used to control the operation of an electrotherapy device in a variety of ways. For example, the second memory may be used to control the operation of the electrotherapy device in a training mode, such as that described in copending U.S. patent application Ser. No. 08/351,897, "Defibrillator With Training Features," filed Dec. 8, 1994. The disclosure of that patent application is incorporated herein by reference.

The second memory may also be used to operate the electrotherapy device in a custom operation mode that differs from an operation mode provided by the first memory. For example, a defibrillator operating with instructions encoded on a first memory to treat adult patients may be transformed into a pediatric defibrillator by attaching a second memory containing instructions used by the controller to treat small children.

Other possibilities include the use of the second memory to operate the electrotherapy device in a patient monitoring mode (in which the device simply monitors a patient but does not deliver an electrical shock), a device self-diagnostic mode (in which the device tests and/or recalibrates itself), a set-up mode (in which certain operation options are selected and activated), or in a code transfer mode (in which instructions in the first memory are replaced with instructions from the second memory). Other possibilities will be apparent to those skilled in the art.

Figure 3:
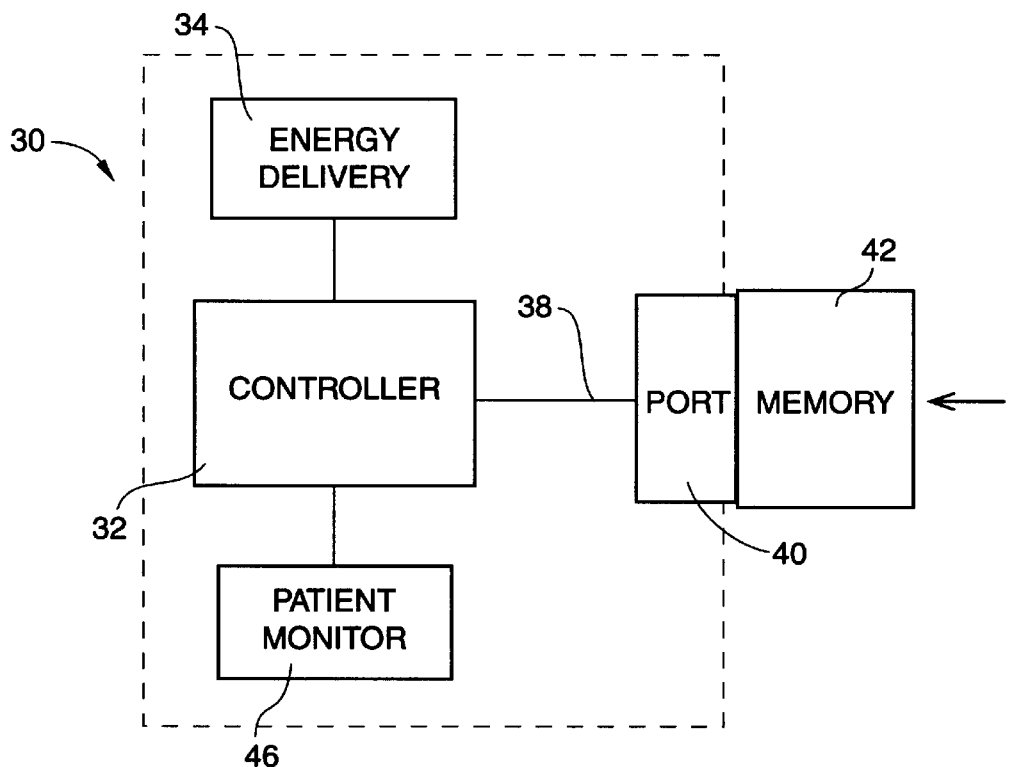
FIG. 3 is a block diagram of an electrotherapy device showing a control system according to another embodiment of this invention.
Figure 4:
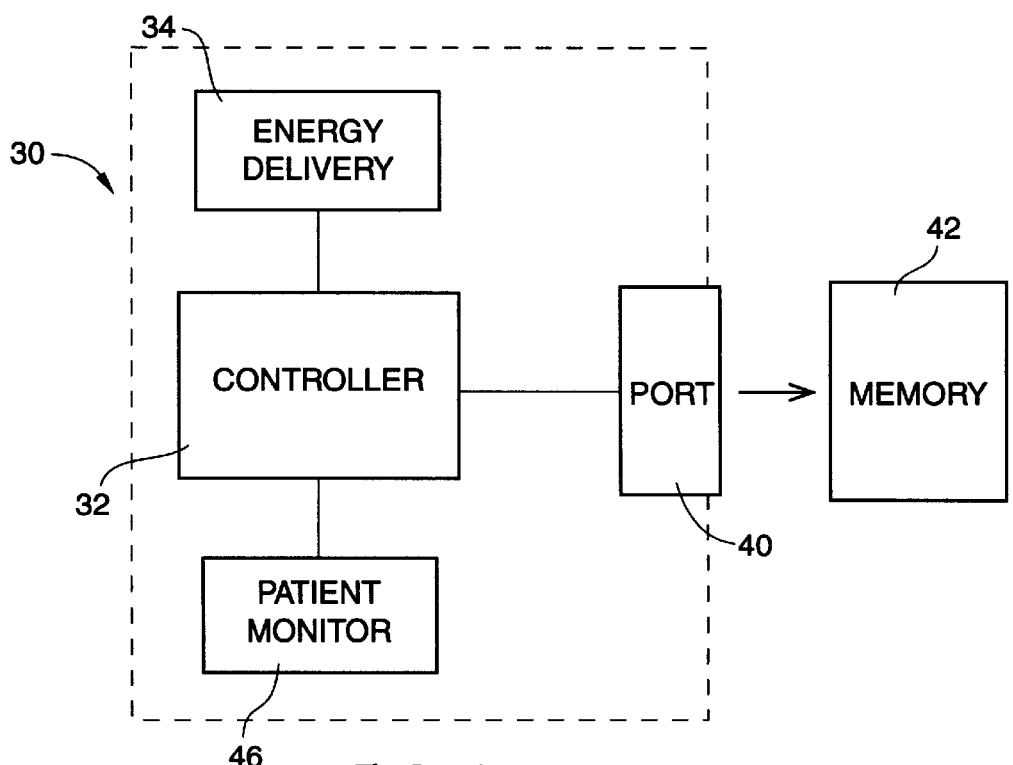
FIG. 4 is a block diagram of the embodiment of FIG. 3 with the memory detached.

Another embodiment of the invention is shown in FIGS. 3 and 4. In this embodiment as in the first embodiment, electrotherapy device 30 has a controller 32 that operates an energy delivery system 34 and performs other aspects of the operation of the device. Device 30 may optionally also include a patient monitor 46. A memory bus 38 extends from controller 32 to a memory port 40 to which a detachable memory 42 has been attached. In this embodiment, however, device 30 has no resident memory from which controller 32 can obtain instructions to operate the device to provide electrotherapy or to perform other electrotherapy device operations. The sole source of controller instructions for operation of the device is memory 42. FIG. 4 shows memory 42 detached from device 30.

Figure 5:
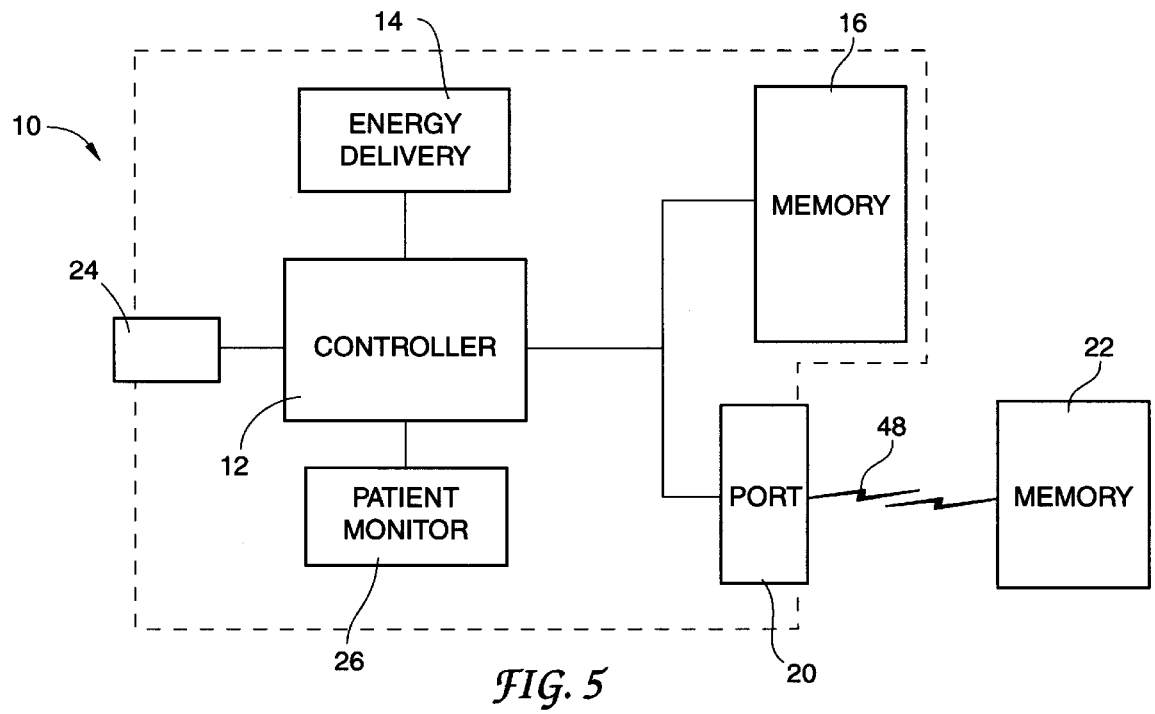
FIG. 5 is a block diagram of the embodiment of FIGS. 1 and 2 showing a remote connection between the second memory and the electrotherapy device.

Alternatively, the second memory of the FIG. 1 embodiment could be disposed at a location remote from device 10 and could communicate the controller's instructions to the device from the remote location through port 20 via a remote connection 48, such as a modem connection, an Ethernet connection, a wireless connection, an ISDN connection, etc. This alternative embodiment is shown in FIG. 5. In this alternative embodiment, remote connection 48 includes all necessary components to provide communication between the memory and the memory port of the electrotherapy device, such as modems for a modem connection and appropriate hardware and software for Ethernet, wireless or ISDN connections. In this embodiment, the remote memory 22 is "attached" to its electrotherapy device when the remote connection is made to permit communication between the remote memory and the device.

The attachable/detachable memories of shown in FIGS. 1–5 may be any suitable memory device known in the art, so long as they can provide the necessary software instructions to the controller at a suitable speed. For example, the memory may be a solid state PC card following the 1995 PC Card format, in which case the memory port would be a PC card slot, as known in the art. Alternatively, other digital memory formats may be used, such as the Minicard format promoted by Intel, Microsoft and others.

Figure 6:
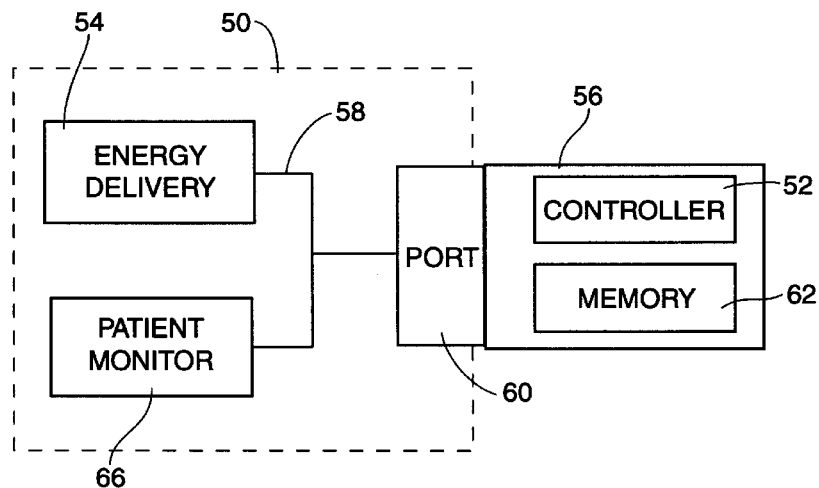
FIG. 6 is a block diagram of another alternative embodiment of the invention.
Figure 7:
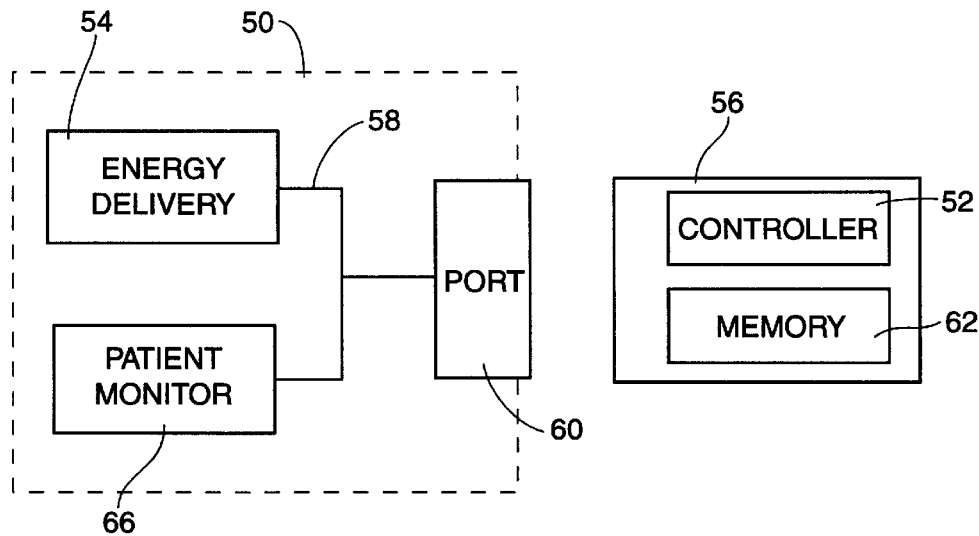
FIG. 7 is a block diagram of the embodiment of FIG. 6 with the memory module detached.

FIGS. 6 and 7 show another alternative embodiment in which the electrotherapy device 50 has no on-board controller. Rather, device 50 operates with a attachable/detachable memory module 56 containing both memory 62 and a controller 52 for operating the electrotherapy device. Memory module communicates with the energy delivery system 54, the optional patient monitoring system 66, and other parts of device 50 via port 60 and bus 58. The operation characteristics of device 50 may be changed and controlled through the attachment of a memory module 56 containing instructions, and a controller, for operating the device in one mode or another.

Preferred embodiments of this invention are described below with reference to external defibrillators. It should be understood that the invention also relates to other electrotherapy devices as well.

Figure 8:
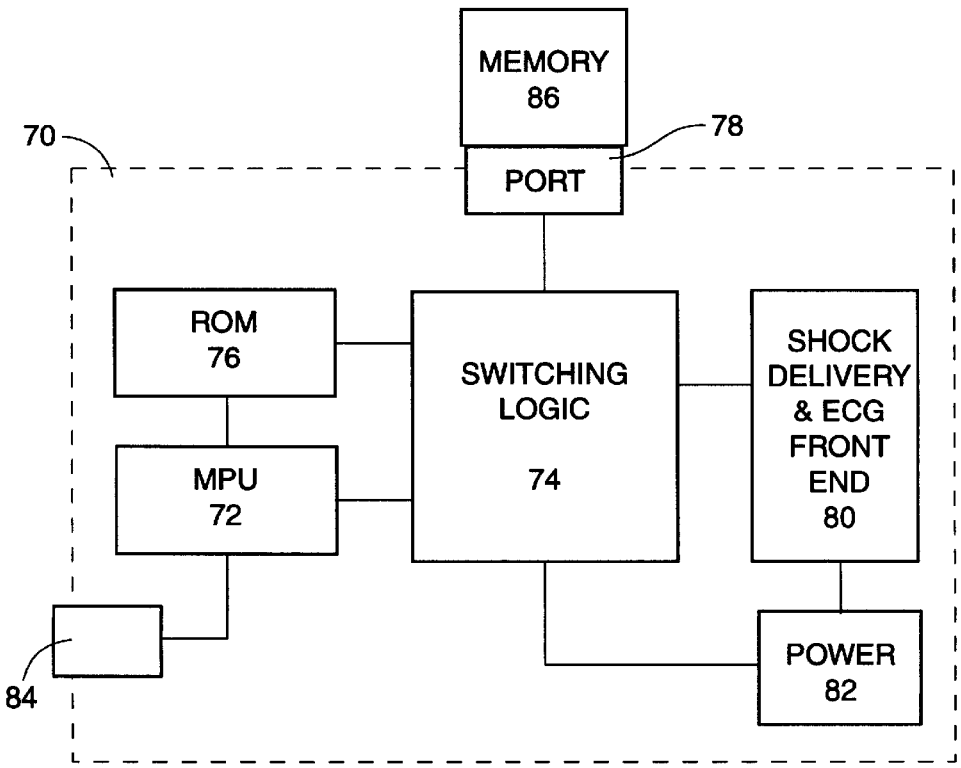
FIG. 8 is a block diagram of an electrotherapy device according to one embodiment of this invention.

FIG. 8 shows an external defibrillator 70 with a microprocessor unit (MPU) 72 performing program steps from software instructions contained in ROM 76. Some of the defibrillator control functions are performed via switching logic 74. For example, logic 74 provides an interface between MPU 72 and a shock delivery and ECG front end module 80 to which defibrillation electrodes and/or monitoring electrodes may be connected. Logic 74 also controls the delivery of energy from a power source 82 to module 80.

A memory port 78 provides an interface between an attachable/detachable memory 86 and switching logic 74. External defibrillator 70 can be operated in different modes; the operational characteristics of defibrillator 70 differ in each mode. The operational characteristics of the defibrillator in any one of the modes can be changed either temporarily or permanently.

For example, external defibrillator 70 can be operated in a patient treatment mode, in which MPU 72 and switching logic 74 interact to treat a patient and, possibly, to record information such as patient ECG and defibrillator operating parameters (e.g., delivery of a shock to the patient) on memory 86. The software instructions controlling MPU 72 in this patient treatment mode and, therefore, the operational characteristics of defibrillator 70, are obtained from ROM 76.

External defibrillator 70 can also be operated in a code-transfer mode. An optional memory control mechanism 84 may be used to change the operation of the defibrillator to code-transfer mode, as discussed above. In this mode, MPU 72 operates solely from software instructions stored in memory 86 to transfer lines of code from memory 86 to ROM 76. This use of software instructions in memory 86 instead of in ROM 76 changes the operational characteristics of defibrillator 70 into code-transfer mode. In addition, the lines of code transferred to ROM 76 will be used in a future defibrillator operation to provide software instructions to MPU 72 for use in operating the defibrillator. Thus, the use of memory port 78 and memory 86 in a code-transfer mode, by changing the software instructions in ROM 76 for future use by MPU 72, changes the operational characteristics of defibrillator 70 in a future use as well.

Yet another operating mode for external defibrillator 70 is a training mode. In training mode, as in code-transfer mode, MPU 72 of external defibrillator 70 obtains its operating instructions solely from memory 86. Training mode simulates the operation of the defibrillator in patient treatment mode without the actual delivery of any shocks to a patient. External defibrillator 70 may enter training mode by actuating a mechanism (such as memory control mechanism 84 or other suitable actuator) or by simply attaching a suitable memory device to port 78.

Figure 9:
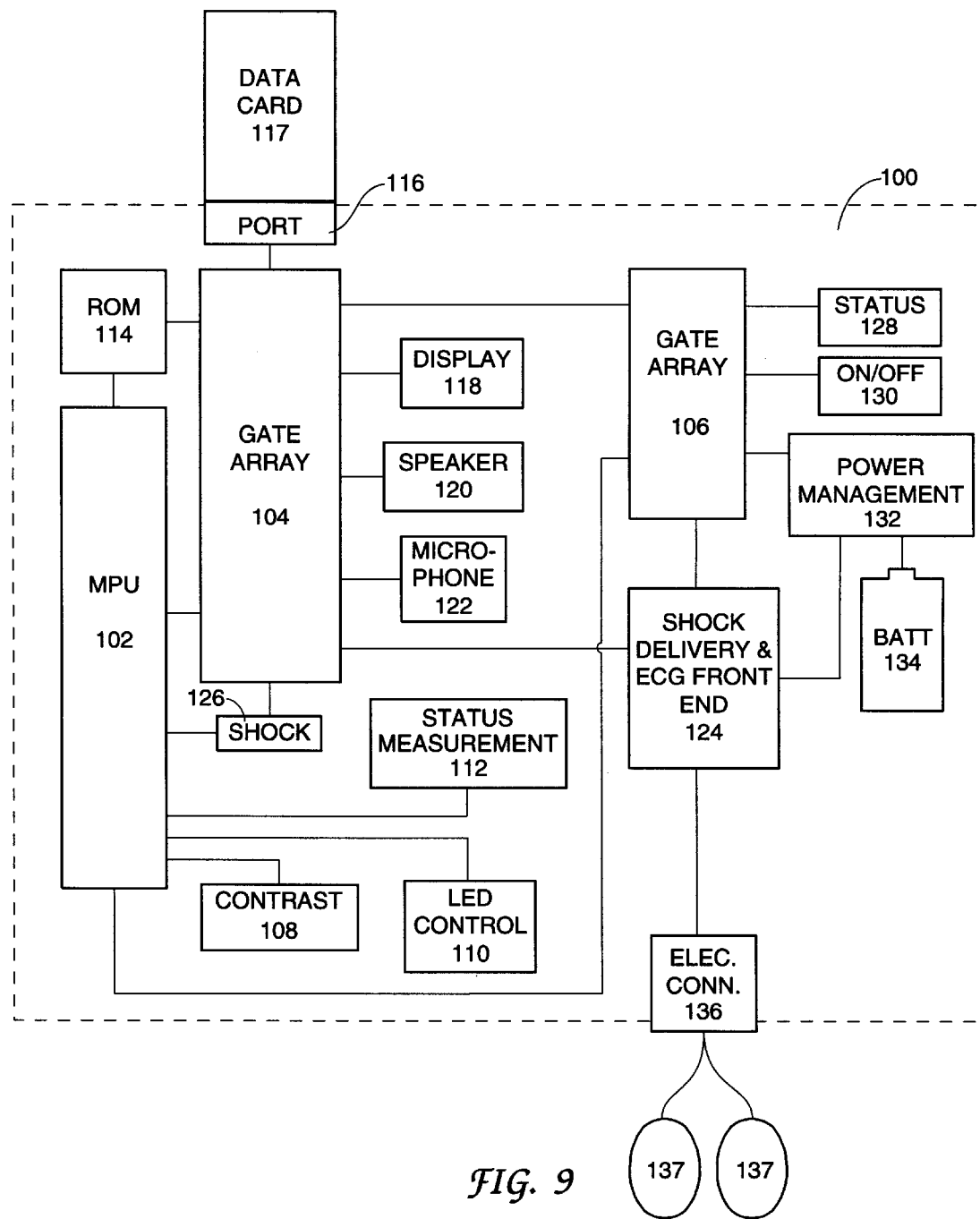
FIG. 9 shows the major components of a semi-automatic external defibrillator in block diagram form.

The major components of a semi-automatic external defibrillator according to a preferred embodiment are shown in FIG. 9 in block diagram form. Defibrillator control functions are divided among a microprocessor unit (MPU) 102 and two custom gate arrays 104 and 106. It should be understood, however, that gate arrays 104 and 106 are optional, and their functions can be performed by other circuits.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114, data card port 116 and other system memory elements. System ROM 114 is preferably flash ROM, although EPROM or any other electrically erasable and programmable nonvolatile memory could be used. Data card port 116 is preferably a data card slot configured to interface with PC data cards conforming to the 1995 PC Card standard.

For purposes of writing to a data card, gate array 104 provides the interface and control between defibrillator 100 and a data card 117 attached to data card port 116. For example, gate array 104 contains a FIFO buffer to compensate for differences between the speed with which ROM 114 can be accessed by MPU 102 and the speed with which the memory portion of data card 117 can be accessed. Gate array 104 also controls a display 118, a speaker 120, and a microphone 122. Gate array 104 can actuate a relay within the shock delivery and ECG front end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in copending U.S. patent application Ser. No. 08/240,272, "Defibrillator With Self-Test Features," filed May 10, 1994, the disclosure of which is incorporated herein by reference. Gate array 106 is also the defibrillator's interface with a user-activated on/off switch 130.

Gate array 106 controls the power management subsystem 132 to provide power to operate system components from battery 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in copending U.S. patent applications Ser. No. 08/103,837, "Electrotherapy Method and Apparatus," filed Aug. 6, 1993, now abandoned, and Ser. No. 08/227,553, "Electrotherapy Method and Apparatus," filed Apr. 14, 1994, now U.S. Pat. No. 5,607,454 the disclosures of which are incorporated herein by reference.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed either temporarily or permanently, as explained below.

Operation of the external defibrillator of this embodiment commences with the insertion of a battery. Once gate array 106 determines that a battery has been inserted to provide power to the defibrillator, gate array 104 prompts MPU 102 to begin its boot sequence. The boot sequence begins with MPU 102 sending out a series of addresses to gate array 104. Unless given instructions to the contrary, the initial MPU addresses to gate array 104 lead MPU to system ROM 114 for the remaining boot sequence.

The defibrillator's initial operation mode when booting from system ROM 114 is self-test mode during which the defibrillator performs an array of self-tests responding to insertion of the battery and possibly to the passage of time or an environmental event. Successful performance of these self-tests places the defibrillator in stand-by mode. The battery insertion self-tests may be terminated before completion by actuating on/off button 130, in which case the defibrillator's displayed status is determined by a shortened self-test sequence.

In stand-by mode, gate array 106 monitors for the presence of system power, the passage of time, temperature or other criteria. Gate array 106 places the defibrillator back into self-test mode when dictated by the passage of a suitable length of time or other criteria. Failure of a self-test may cause the gate array 106 to place the defibrillator in an inoperable mode, in which case gate array indicates the inoperable status of the defibrillator through status display 128 and possibly other means.

When defibrillator 100 is in stand-by mode, actuation of on/off button 130 causes MPU 104 to begin receiving instructions from system ROM 114 to operate the defibrillator in a mode dictated by the instructions present in ROM 114. For example, provided that suitable instructions are present in ROM 114, actuation of on/off button 130 will place defibrillator 100 in patient treatment mode after successful completion of the defibrillator's power-on self-tests. In patient treatment mode, defibrillator 100 can (1) determine whether electrodes are attached to electrode connector 136, (2) receive ECG information from a patient through such electrodes, (3) analyze the ECG information to determine whether a therapeutic shock is advised, and (4) deliver a shock to the patient through the electrodes if a shock is advised and if the shock button 126 is actuated by a user. Defibrillator 100 can also store information regarding the patient (such as ECG information), the defibrillator (such as defibrillator operation information) and other information (such as ambient sounds received by microphone 122) on a patient data card attached to data card port 116.

Figure 10:
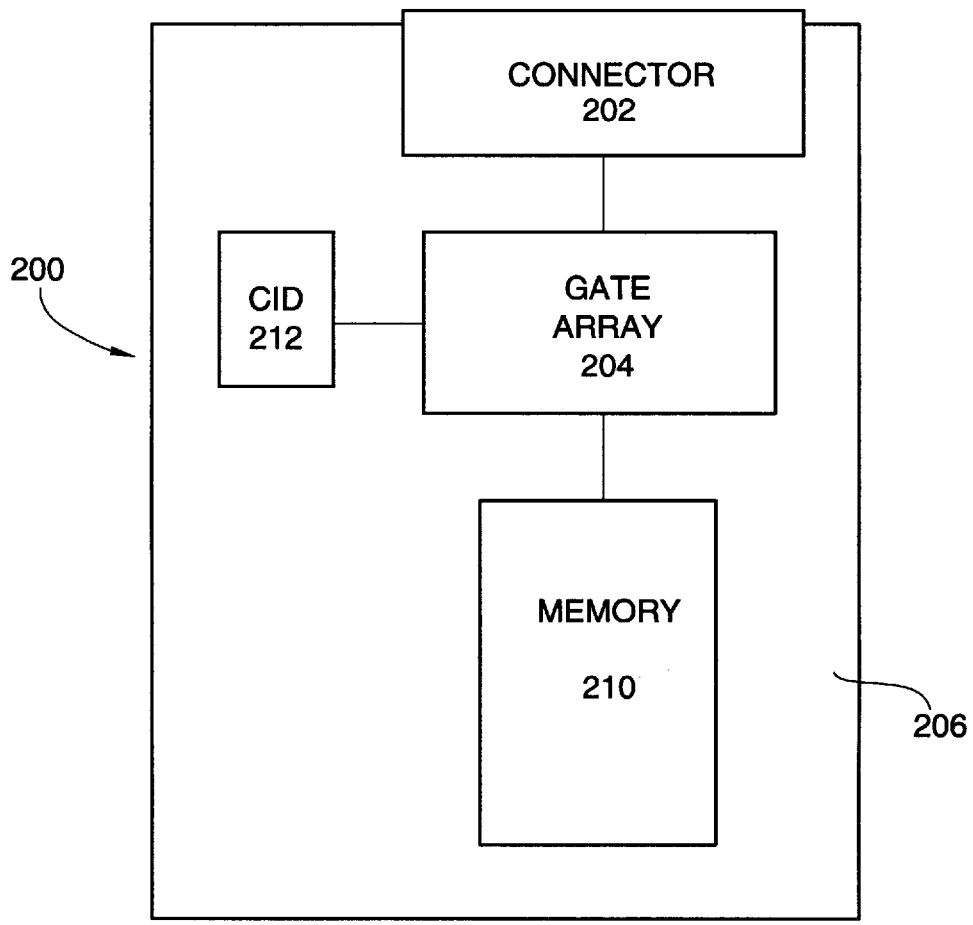
FIG. 10 is a block diagram of a data card following the 1995 PC Card Standard for use with the defibrillator shown in FIG. 9.

FIG. 10 is a block diagram of a data card following the 1995 PC Card Standard for use with the defibrillator shown in FIG. 9. Data card 200 has a connector 202 communicating with a gate array 204 over a suitable bus. The 1995 PC Card Standard defines three memory spaces: common, I/O, and attribute. Gate array 204 contains card attribute memory. Gate array 204 also communicates with a solid state memory 210, and a card identification ("CID") source 212. Memory 210 conforms to common or I/0 memory as defined in the 1995 PC Card Standard. Each of these elements is disposed in a card housing 206.

The operational characteristics of defibrillator 100 can be controlled by a data card in several ways. In one embodiment, MPU 102 can be operated using instructions obtained solely from a data card attached to data card port 116 without using instructions from system ROM 114. With reference to FIG. 10, after the boot sequence responding to battery insertion (described above), the instructions in system ROM 114 instruct MPU to read the CID 212 of any data card that might be attached to port 116. If the CID identifies the data card as one containing executable code or instructions, MPU ceases receiving instructions from system ROM 114 and begins executing instructions taken from the data card memory 210.

Thus, for example, by providing a suitable identification on CID 212 and suitable code in memory 210, defibrillator 100 will begin obtaining its operating instructions solely from the data card to be operated in a training mode in which the defibrillator merely simulates the operation of the defibrillator in patient treatment mode without the actual delivery of any shocks through electrode connector 136. Operation in this training mode continues until the defibrillator is turned off, the power is cut off, or the training data card is removed.

This approach may also be used to operate the defibrillator in a custom operation mode. For example, the data card may contain instructions to operate the defibrillator to provide a treatment that differs from the treatment the defibrillator would provide in its normal patient treatment mode, to, e.g., provide shocks at different energy levels or different time intervals. This customization could also include operating the device not as a defibrillator but as a cardioverter or as an external pacer. In each of these cases the device would operate solely from software instructions contained in the data card memory after initially booting from internal memory.

Figure 11:
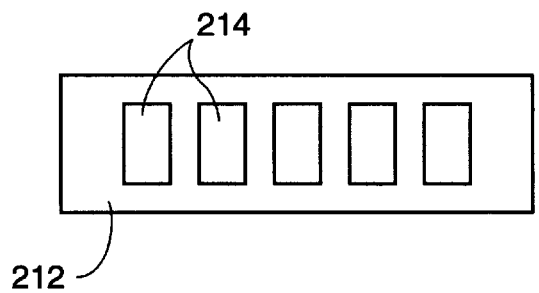
FIG. 11 shows a preferred card identification for use with the data card shown in FIG. 10.

In a preferred embodiment, CID 212 is a series of coding resistors 214, as shown schematically in FIG. 11, which can be read through gate array 204. Unique combinations of the coding resistors (i.e., whether a given resistor is "loaded" or not "loaded") identify the data card as a recording memory unit, (such as patient data card for storing patient and defibrillator information), an executing memory unit (such as a data card containing executable code for operating the defibrillator), or any other type of data card that the device is designed to use. Other ways of distinguishing one type of data card from another may be used, of course, without departing from the scope of the invention, such as DIP switches or other binary representation.

The data card can also be used to operate the defibrillator in a code-transfer mode. In this mode, the defibrillator actually boots from code stored in data card memory and not from code within defibrillator system ROM. After booting, the MPU operates solely from instructions contained within data card memory to transfer software code from data card memory to defibrillator system ROM. Defibrillator system ROM is preferably flash memory to facilitate this transfer, although system ROM could be EPROM or any other electrically erasable and programmable nonvolatile memory. After the transfer is complete, the final instruction from the data card causes the defibrillator to transfer execution to, or reboot from, system ROM and to operate from instructions contained in system ROM.

It also possible to boot from the data card in operation modes other than code transfer mode, of course.

Figure 12:
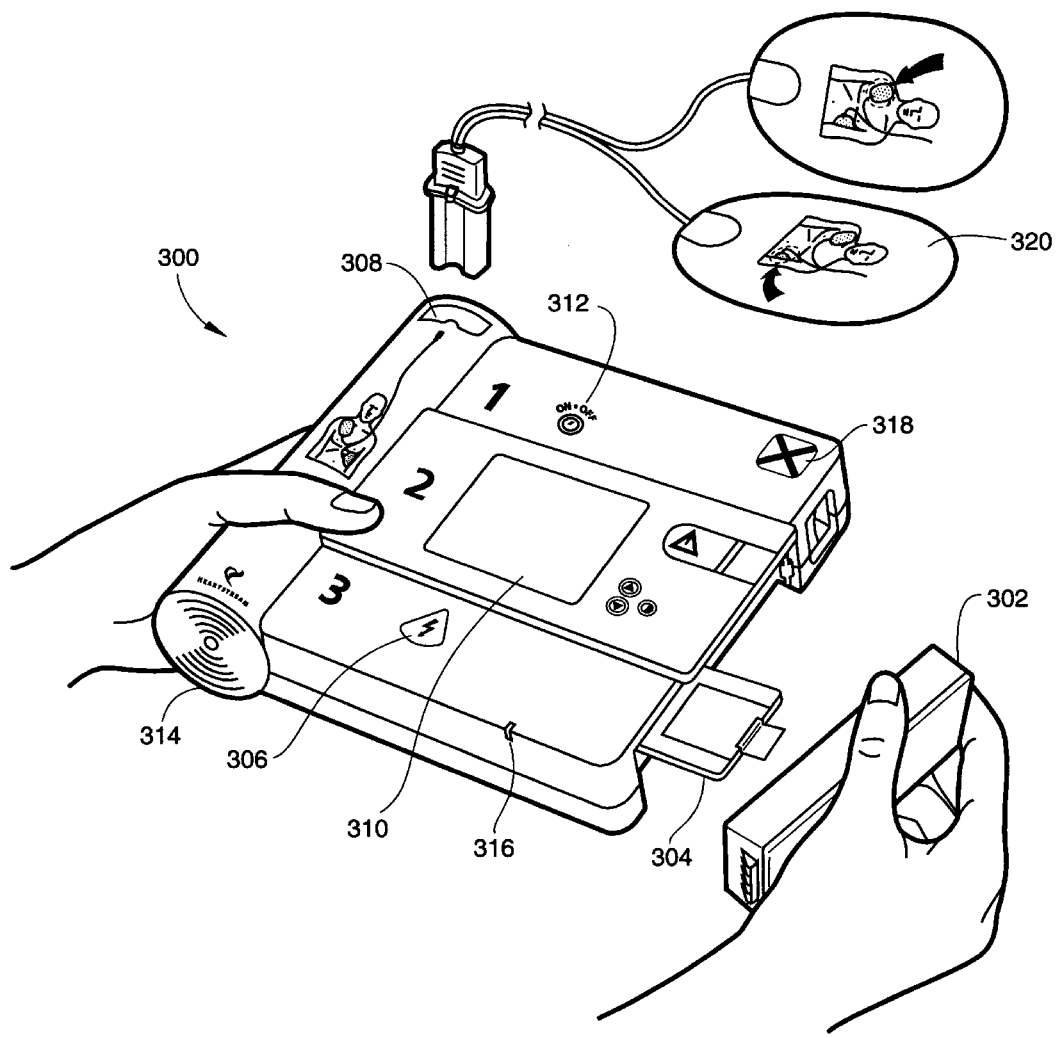
FIG. 12 is a perspective view of a defibrillator showing a preferred arrangement of a data card slot and battery pack.

One example of a code-transfer data card is one that changes the defibrillator's operating language (i.e., the language in which the defibrillator displays and/or announces instructions or results) from one language to another (e.g., from English to German). Thus, the defibrillator of FIG. 9 could be modified so as to operate in a patient treatment mode in which the display 118 displays instructions and other information, and the speaker 120 announces instructions and other information, in German instead of English, by rewriting the MPU's treatment mode instructions in system ROM 102. Another example is the use of code-transfer mode as a manufacturing step to write operating code to the defibrillator's internal ROM for the first time. As a safeguard against inadvertent rewriting of the defibrillator's system ROM, an actuation sequence is preferably performed before entering code-transfer mode. For example, in one embodiment the data card slot of defibrillator 300 is located behind the defibrillator battery pack 302 when the battery pack is loaded into the defibrillator. FIG. 12 shows the battery pack 302 removed from the defibrillator and the data card 304 extending from the data card slot (not shown). After inserting a code-transfer data card (such as data card 304 in FIG. 11) into the defibrillator's data card slot, the user must depress the "Shock" button 306 on the defibrillator as the battery pack 302 is inserted. On power-up, the system gate array detects (1) the presence of a data card in the data card slot, (2) the presence of a battery pack and (3) the depression of "Shock" button 306 and changes the routing of the MPU's initial address signal from system ROM to the data card slot. The process then proceeds as outlined above.

Other methods may be used to safeguard against inadvertent rewriting of defibrillator memory. For example, in addition to some kind of manual actuation sequence performed by a defibrillator operator, the data card itself could contain a specific code or sequence in its memory. Detection by the MPU of the presence of such a sequence on the data card memory could be a precondition to the transfer of code or other information from the data card to the defibrillator system ROM. Other safeguards will be apparent to those skilled in the art.

The CID can also be used to identify a patient data card. When a patient data card is present, the defibrillator operates in its patient treatment mode, as described above, and stores patient information, defibrillator operation information (such as shock delivery and self-test results) and other information. The defibrillator also preferably stores time information along with this patient, defibrillator and other information. A preferable method for recording time is to incorporate a clock on the patient data card, as discussed in copending U.S. patent application Ser. No. 08/314,395, "Method and Apparatus for Gathering Event Data Using a Removable Data Storage Medium and Clock," filed Sep. 28, 1994, now U.S. Pat. No. 5,549,115, the disclosure of which is incorporated herein by reference.

Also shown in FIG. 12 are the defibrillator's electrode connector 308, display 310, on/off button 312, speaker 314, microphone 316, and status display 318. Electrodes 320 for use with the defibrillator are also shown.

It is possible to operate the defibrillator in a mode in which the MPU takes some of its operating instructions from internal ROM and some from an attached data card. For example, in training mode, the controller may take its defibrillator simulation instructions from the data card but may also use subroutines within internal ROM for the procedures of issuing voice prompts at appropriate points in the simulation or for operating the display. The invention is intended to cover all operating modes where at least some of the instructions used by the MPU come from an attached data card instead of from system ROM.

Figure 13:
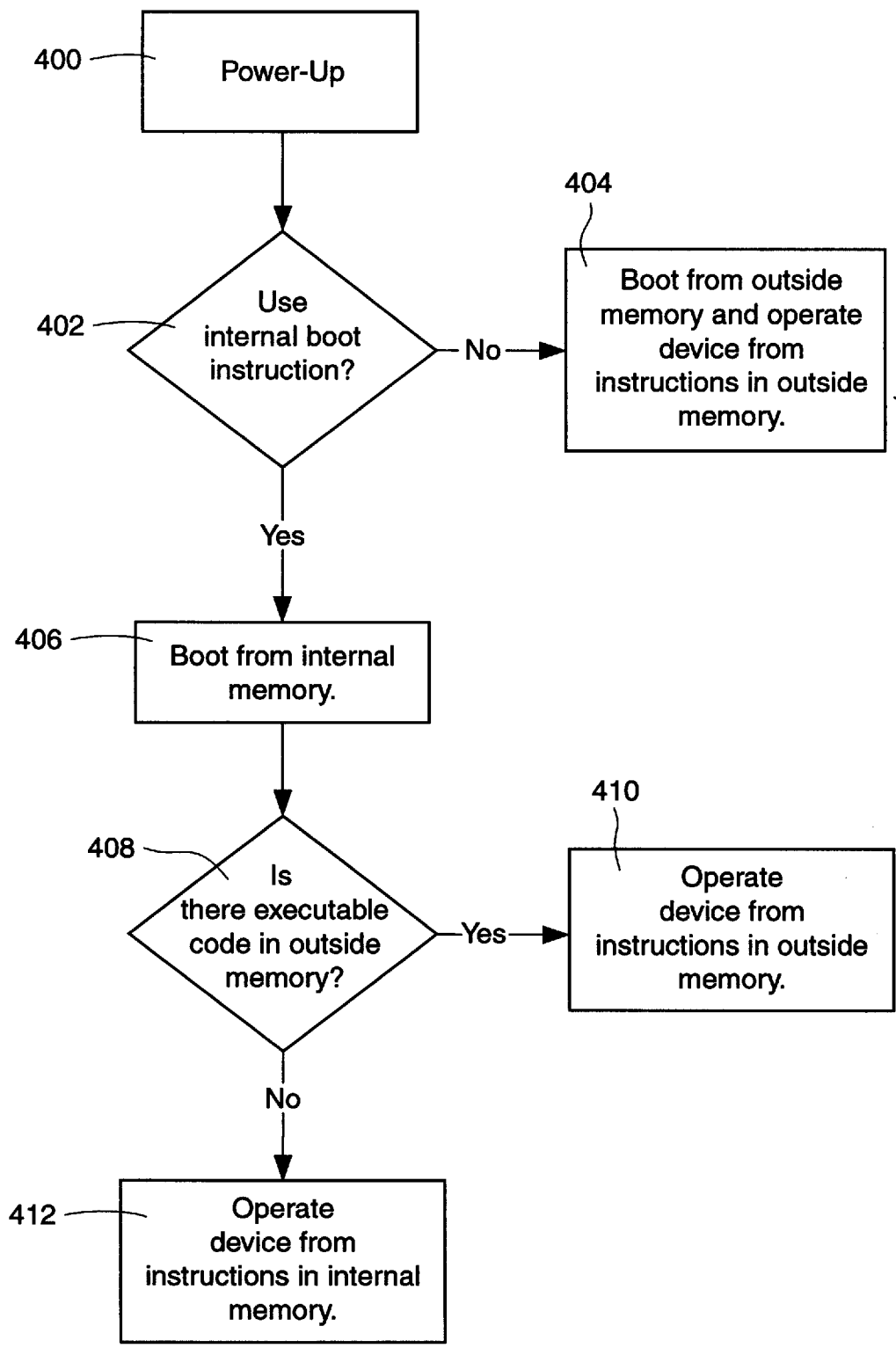
FIG. 13 is a flow chart summarizing preferred methods of controlling the operating characteristics of an electrotherapy device.

FIG. 13 is a flow chart summarizing these methods of controlling the operating characteristics of an electrotherapy device. The initial step 400 is the step of powering-up the device. After power-up, the device determines at decision block 402 whether it should use internal boot instructions. If not, then the device boots directly from instructions contained in an outside memory that has been attached to the device and thereafter operates from instructions contained in the outside memory, as indicated by block 404. The device's operation may be controlled solely by instructions contained in the outside memory, such as in the code-replacement mode described above. Alternatively, the device's controller may take only part of its software code or instructions from the outside memory. If, on the other hand, the device determines that it should boot from instructions contained in internal memory, it does so, as in block 406.

If the device has booted from internal memory, it must determine whether to take all of its instructions from internal memory or whether to look to an attached outside memory to obtain some or all of its instructions, i.e., the device must determine whether there is executable code in an attached outside memory. This determination and the alternative outcomes are shown in blocks 408–412. As before, if there is executable code in an attached outside memory, the device's controller may take some or all of its instructions from the outside memory.

Figure 14:
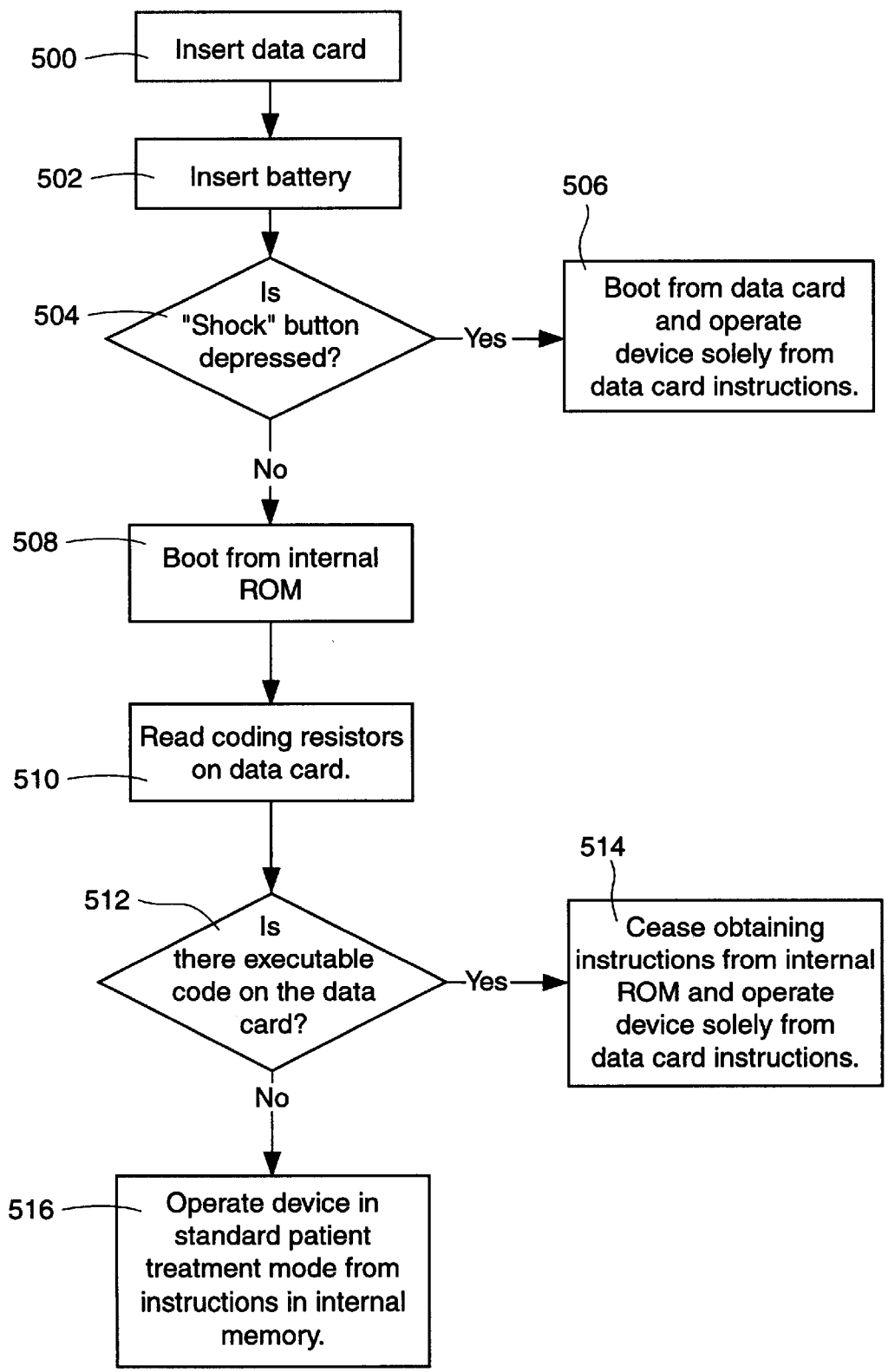
FIG. 14 shows one specific application of a preferred method to the external defibrillator described with reference to FIGS. 9 and 12.

FIG. 14 shows one specific application of this method to the external defibrillator described with reference to FIGS. 9 and 12. The process begins with insertion of a data card and insertion of the defibrillator's battery pack, as shown in blocks 500 and 502. If the defibrillator's "Shock" button is depressed as the battery pack is inserted, then the defibrillator proceeds to boot from code on the data card, as shown in blocks 504 and 506. More specifically, with reference to FIG. 8, system gate array 104 detects the operation of shock button 126 during insertion of the battery pack and changes the location from which MPU 102 will obtain boot instructions from system ROM 114 to data card port 116. After booting, the defibrillator will then operate from instructions taken from the data card. If, on the other hand, the shock button is not depressed during insertion of the battery pack, the defibrillator will boot from instructions contained in system ROM 114.

After booting, in order to determine whether there is executable code on the data card, the defibrillator reads the coding resistors in the CID portion of the data card, as in block 510. If there is executable code on the data card, the defibrillator's MPU ceases to obtain instructions from system ROM 114 and begins obtaining instructions from the data card, as in block 514. If, however, the data card does not contain executable code, the defibrillator operates in its standard patient treatment mode, which may include recording patient information and/or defibrillator operation information on the data card, as shown in block 516.

Modifications to the invention will be apparent to those skilled in the art.

What is claimed is:

1. A method of controlling the operation characteristics of an electrotherapy device comprising:

providing an electrotherapy device having a controller and a first memory, the first memory containing instructions for use by the controller to operate the electrotherapy device;

attaching a second memory to the electrotherapy device without detaching the first memory from the electrotherapy device, the second memory containing instructions for use by the controller to operate the electrotherapy device; and operating the electrotherapy device using instructions from the second memory.

2. The method of claim 1 wherein the operating step comprises operating the electrotherapy device in a training mode.

3. The method of claim 1 wherein the operating step comprises operating the electrotherapy device in a treatment mode.

4. The method of claim 1 wherein the operating step comprises operating the electrotherapy device in a custom operation mode.

5. The method of claim 1 wherein the operating step comprises operating the electrotherapy device in a diagnostic mode.

6. The method of claim 1 wherein the operating step comprises operating the electrotherapy device in a patient monitoring mode.

7. The method of claim 1 wherein the operating step comprises operating the electrotherapy device in a set-up mode.

8. The method of claim 1 wherein the operating step comprises operating the electrotherapy device in code transfer mode to replace instructions in the first memory with instructions in the second memory.

9. The method of claim 1 wherein the operating step comprises providing information to a user in a language controlled by instructions contained in the second memory.

10. The method of claim 1 further comprising, prior to the operating step, actuating a memory control mechanism to transfer communication between the controller and the first memory to communication between the controller and the second memory.

11. The method of claim 1 wherein the attaching step comprises inserting a second memory into the device.

12. The method of claim 1 wherein the attaching step comprises providing communication between the second memory and the electrotherapy device, the second memory being disposed at a location remote from the electrotherapy device.

13. The method of claim 1 wherein the attaching step comprises attaching the second memory to a memory port in the electrotherapy device.

14. The method of claim 13, prior to the attaching step, further comprising the step of operating the electrotherapy device using instructions contained only in the first memory to write information to the memory port.

15. The method of claim 1 wherein the electrotherapy device is a defibrillator, the first memory containing instructions for use by the controller to operate the defibrillator in a treatment mode to treat a patient.

16. The method of claim 1 further comprising booting the electrotherapy device from instructions contained in the first memory.

17. The method of claim 1 further comprising booting the electrotherapy device from instructions contained in the second memory.

18. The method of claim 1 further comprising determining whether there are executable instructions in the second memory.

19. The method of claim 18 wherein the determining step comprises reading an identification in the second memory.

20. The method of claim 1 wherein the operating step further comprises operating the electrotherapy device using instructions from the first memory.

21. A method of operating an electrotherapy device comprising:
attaching a memory to a memory port in a housing of the electrotherapy device; and
reading instructions from the memory to operate the electrotherapy device.

22. The method of claim 21 wherein the attaching step comprises inserting a PC card into a card slot in the electrotherapy device.

23. A control system for an electrotherapy device comprising:

a controller;
a first memory communicating with the controller, the first memory containing instructions for use by the controller to operate the electrotherapy device; and
a second memory communicating with the controller via a memory port, the second memory containing instructions for use by the controller to operate the electrotherapy device without instructions from the first memory.

24. The control system of claim 23 further comprising means for transferring communication between the controller and the first memory to communication between the controller and the second memory.

25. The control system of claim 24 wherein the means for transferring comprises a memory control mechanism.

26. The control system of claim 25 wherein the memory control mechanism comprises a button.

27. The control system of claim 25 wherein the memory control mechanism comprises an actuator responsive to the attachment of the second memory to the memory port.

28. The control system of claim 24 wherein the means for transferring comprises instructions causing the controller to communicate with the second memory.

29. The control system of claim 23 wherein the controller and the first memory comprise means for writing information to the memory port.

30. A control system for an electrotherapy device comprising:
a controller;
a first memory communicable with the controller, the first memory containing instructions for use by the controller to operate the electrotherapy device; and
means for establishing communication between the controller and a second memory without removing the first memory from the electrotherapy device and for operating the electrotherapy device using instructions from the second memory without using instructions from the first memory.

31. An electrotherapy device comprising:
a controller;
an energy delivery system communicable with the controller; and
a first memory communicable with the controller, the first memory containing instructions for use by the controller to operate the electrotherapy device;
the controller comprising means for establishing communication between the controller and a second memory without removing the first memory from the electrotherapy device and for operating the electrotherapy device using instructions from the second memory without using instructions from the first memory.

32. The electrotherapy device of claim 31 further comprising a memory port, the means for establishing communication comprising means for establishing communication with the memory port.

33. The electrotherapy device of claim 32 wherein the memory port comprises a PC card slot.

34. The electrotherapy device of claim 31 further comprising a memory control mechanism.

35. An electrotherapy device comprising:
a controller;
an energy delivery system communicable with the controller; and
a memory port;
the controller comprising means for establishing communication between the controller and a memory attached to the memory port and for operating the electrotherapy device using instructions from the memory.

36. A memory device for use with an electrotherapy device comprising:

a housing; a connector adapted to connect with a memory port of an electrotherapy device; memory comprising instructions for operating an electrotherapy device; control logic; and a memory device identification.

37. A method of operating an electrotherapy device comprising the following steps:

attaching a memory unit to a memory unit port in the electrotherapy device; and determining whether the memory unit is a recording memory unit to which information may be written by the electrotherapy device and whether the memory unit is an executing memory unit from which executable code may be obtained by the electrotherapy device.

38. The method of claim 37 wherein the determining step comprises reading a memory unit identification.

39. The method of claim 37 further comprising, after the determining step, writing information to the memory unit if the memory unit is determined to be a recording memory unit.

40. The method of claim 37 further comprising, after the determining step, obtaining operating instructions from the memory unit if the memory unit is determined to be an executing memory unit.

41. An electrotherapy device comprising:

an energy source;

an electrode interface;

a controller operatively connected with the energy source and the electrode interface to deliver energy from the energy source to the electrode interface;

a memory port;

the controller comprising means for determining whether a memory unit attached to the memory port is a recording memory unit to which information may be written by the controller and whether the memory unit is an executing memory unit from which execution code may be obtained by the controller.

42. The electrotherapy device of claim 41 wherein the controller further comprises means for writing information to a memory unit attached to the memory port if the memory unit is determined to be a recording memory unit.

43. The electrotherapy device of claim 41 wherein the controller further comprises means for obtaining operating instructions from a memory unit attached to the memory port if the memory unit is determined to be an executable memory unit.

44. The electrotherapy device of claim 41 wherein the means for determining comprises means for reading a memory unit identification from a memory unit attached to the memory port.

45. A memory unit for use with an electrotherapy device, the memory unit comprising:

a connector;

digital memory storage;

a memory unit identification identifying the memory unit as a recording memory unit to which information may be written by an electrotherapy device to which the memory unit is attached or as an executing memory unit from which executable code may be obtained by the electrotherapy device; and a bus communicating the digital memory storage and the memory unit identification to the connector.

46. A method of controlling the operation characteristics of an electrotherapy device comprising:

providing an electrotherapy device having a controller and a first memory, the first memory containing instructions for use by the controller to operate the electrotherapy device;

attaching a second memory to the electrotherapy device, the second memory containing instructions for use by the controller to operate the electrotherapy device; and operating the electrotherapy device in code transfer mode to replace instructions in the first memory with instructions in the second memory.

* * * * *